(12) United States Patent
Phillips et al.

(10) Patent No.: US 10,058,693 B2
(45) Date of Patent: Aug. 28, 2018

(54) INTERLOCK FEED SET COUPLING

(71) Applicant: Applied Medical Technology, Inc., Brecksville, OH (US)

(72) Inventors: Grant Wesley Phillips, Richfield, OH (US); Derek M. Williams, Cuyahoga Falls, OH (US)

(73) Assignee: APPLIED MEDICAL TECHNOLOGY, INC., Brecksvillle, OH (US)

( * ) Notice: Subject to any disclaimer, the term of this patent is extended or adjusted under 35 U.S.C. 154(b) by 205 days.

(21) Appl. No.: 14/286,459

(22) Filed: May 23, 2014

(65) Prior Publication Data
US 2015/0335874 A1    Nov. 26, 2015

(51) Int. Cl.
*A61M 39/10* (2006.01)
*A61M 39/26* (2006.01)
*A61J 15/00* (2006.01)
*A61M 39/00* (2006.01)

(52) U.S. Cl.
CPC ...... *A61M 39/1011* (2013.01); *A61J 15/0015* (2013.01); *A61J 15/0026* (2013.01); *A61J 15/0042* (2013.01); *A61J 15/0057* (2013.01); *A61J 15/0092* (2013.01); *A61M 39/26* (2013.01); *A61M 2039/0009* (2013.01); *A61M 2039/1061* (2013.01); *A61M 2039/1072* (2013.01); *A61M 2039/1077* (2013.01)

(58) Field of Classification Search
CPC .............. A61M 39/1011; A61M 39/26; A61M 2039/1077; A61M 2039/1072; A61M 2039/1061; A61M 2039/0009; A61J 15/0057; A61J 15/0026; A61J 15/0042; A61J 15/0015; A61J 15/0092
See application file for complete search history.

(56) References Cited

U.S. PATENT DOCUMENTS

| | | | |
|---|---|---|---|
| 6,878,130 B2 * | 4/2005 | Fournie | A61J 15/0015 604/100.01 |
| 8,449,528 B2 | 5/2013 | Griffith et al. | |
| 8,707,950 B1 * | 4/2014 | Rubin | A61M 16/06 128/200.24 |

(Continued)

FOREIGN PATENT DOCUMENTS

WO    02/066108 A1    8/2002

OTHER PUBLICATIONS

International Search Report from Corresponding Application No. PCT/US2015/028387; dated Aug. 3, 2015.

(Continued)

*Primary Examiner* — Lauren P Farrar
(74) *Attorney, Agent, or Firm* — Pearne & Gordon, LLP (57) ABSTRACT

An interlock coupling adapter for delivering medical fluids to a patient, for example, with enteral feed set devices is provided herein. The interlock coupling adapter increases patient comfort and ensures a secure connection between a button/button base and a food source or medical fluid source. The interlock coupling adapter has an interlock inset within an opening of a button base. The interlock has a recess in which locking protrusions of an adapter may fit within. In this way, the adapter may freely rotate about the interlock. The adapter may be connected or disconnected by depressing flexible arms hinged to the adapter.

8 Claims, 6 Drawing Sheets

(56) References Cited

U.S. PATENT DOCUMENTS

| | | | |
|---|---|---|---|
| 2003/0225376 A1 | 12/2003 | Fournie | |
| 2005/0090805 A1* | 4/2005 | Shaw | A61M 39/26 604/523 |
| 2006/0052752 A1 | 3/2006 | McMichael | |
| 2006/0129090 A1* | 6/2006 | Moberg | A61M 5/158 604/93.01 |
| 2007/0276356 A1* | 11/2007 | Downing | A61M 39/12 604/535 |
| 2009/0287156 A1* | 11/2009 | Regnault | A61J 15/0057 604/174 |
| 2010/0185159 A1* | 7/2010 | Bagwell | A61M 39/1055 604/256 |
| 2012/0029483 A1 | 2/2012 | Griffith | |
| 2013/0296832 A1* | 11/2013 | Griffith | A61J 15/0015 604/535 |
| 2014/0031754 A1 | 1/2014 | Williams | |

OTHER PUBLICATIONS

Extended European Search Report dated Jan. 9, 2018 for corresponding European Application No. 15796990.8.

* cited by examiner

INTERLOCK FEED SET COUPLING

FIELD OF THE INVENTION

The invention described herein relates to an interlock coupling adapter for delivering medical fluids to a patient. More specifically, the invention described herein relates to an interlock coupling adapter for enteral feed set devices.

BACKGROUND OF THE INVENTION

Various medical conditions make it difficult or impossible for some people to eat. In these cases, gastrostomy tubes are a convenient, comfortable, and effective means for delivering nutritional formulas to the body. During a gastrostomy procedure, a stoma is formed in the stomach or intestinal wall and a catheter is placed therein. Feeding solutions may then be fed to the patient through a feeding tube connected to the catheter. This process is known as enteral feeding.

To increase comfort, a number of low-profile catheters have been developed, which sit on or near the patient's skin. However, such a configuration makes it difficult to connect the feeding tube, particularly at night time or for larger patients. Because feeding can often take several hours, it is important to ensure the connection between the feeding tube and the catheter is secure to prevent leaking when a patient moves. In addition to the patient not receiving the appropriate nutrition, such leaking can cause irritation around the stoma.

Currently, connection adapters are notched or keyed such that the notches of the feeding tube and the catheter must be aligned and then twisted, or locked, into place. Such designs are not flexible to the movement of the patient and can be difficult to align in the dark. Other designs require the protrusion of a locking device from the catheter, which can decrease patient comfort and mobility. Still other designs include snap connectors, which require forceful pushing and pulling on the catheter and feeding tubes to connect or disconnect. Such force may cause irritation or removal of the catheter from the stoma.

Accordingly, the invention described herein is intended to address these and similar problems associated with enteral feeding, and more general, the delivery of medical fluids to patients.

BRIEF SUMMARY OF THE INVENTION

A simplified summary is provided herein to facilitate a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

According to one non-limiting example, an interlock adapter connector for providing a medical fluid to a patient comprises a rigid body, and the rigid body comprises an input port, an output port, and a pathway between the input and output ports through which the medical fluid may flow through the rigid body; and at least two hinges extending from the rigid body and at least two flexible arms that extend from the at least two hinges and are continuous with the rigid body on one end and comprise a locking protrusion at an opposite end, wherein when the flexible arms are depressed radially inward about the hinges, the locking protrusions of the flexible arms also rotate radially inward about the hinge.

In various embodiments, the above described interlock adapter connector may have a rigid body that is made from plastic; the at least two flexible arms may comprise ridges on an outer surface of each flexible arm for increasing a user's grip; the pathway may be bent or curved between the input and output ports; the pathway may be straight between the input and output ports; the interlock adapter may be comprised of separately molded pieces or by a single molded piece; and/or the interlock adapter connector comprises a material that glows in the dark.

According to another non-limiting example, an interlock adapter connector for providing a medical fluid to a patient comprises a catheter base with an opening; and an interlock inset in the opening, wherein the interlock comprises an opening through which the medical fluid may flow into the opening of the catheter base and an inner wall of the interlock formed by said opening contains a recess circumferentially around the opening.

In various embodiments, the catheter base may be manufactured with the interlock inset in the opening of the catheter base; the interlock may be manufactured separately from the catheter base; the interlock may be made from at least one of plastic or other suitable material and the catheter base is made from at least one of silicone or other biologically suitable material; and/or the interlock adapter connector may comprise a material that glows in the dark.

In still another non-limiting example, an interlock adapter connector for providing a medical fluid to a patient comprises a rigid body, the rigid body comprising an input port, an output port, and a pathway between the input and output ports through which the medical fluid flows through the rigid body; and at least two flexible arms extending from the rigid body creating a hinge on one end and comprising a locking protrusion at an opposite end, wherein when the flexible arms are depressed radially inward about the hinge, the locking protrusions of the flexible arms also rotate radially inward about the hinge; a catheter base with an opening; and an interlock inset in the opening of the catheter base, wherein the interlock comprises an opening through which the medical fluid flows into the opening of the catheter base, and an inner wall of the interlock formed by said opening contains a recess circumferentially around the opening, and wherein the rigid body is capable of mating with the interlock such that the locking protrusions sit within the recess of the interlock and the locking protrusions rotate freely when mated.

In various embodiments, depressing the at least two flexible arms releases the rigid body from the interlock; the rigid body and interlock may be made from plastic and the catheter base may be made from silicone; the interlock adapter connector comprises a material that glows in the dark; upon mating, the output port may penetrate a valve located within the catheter base; and/or the rigid body may be comprised by separately molded pieces.

These and other embodiments are described in more detail below.

DETAILED DESCRIPTION OF THE DRAWINGS

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

The device described herein relates to an interlock coupling adapter for delivering medical or nutritional fluids to a patient, for example, in association with enteral feed set devices. While the device is illustrated and described herein with respect to enteral feeding, it should be noted that this is not intended to be a limiting use. For example, the term medical fluid may pertain to any of, or combination of, liquids and gases associated with medicine, physiology, and the like. That is, the present invention can apply to the delivery of medications in solution, delivery of food or other nutritional supplements, the delivery of oxygen, or the venting of gas from the stomach or other part of the body where a stoma is present.

Figure 1:
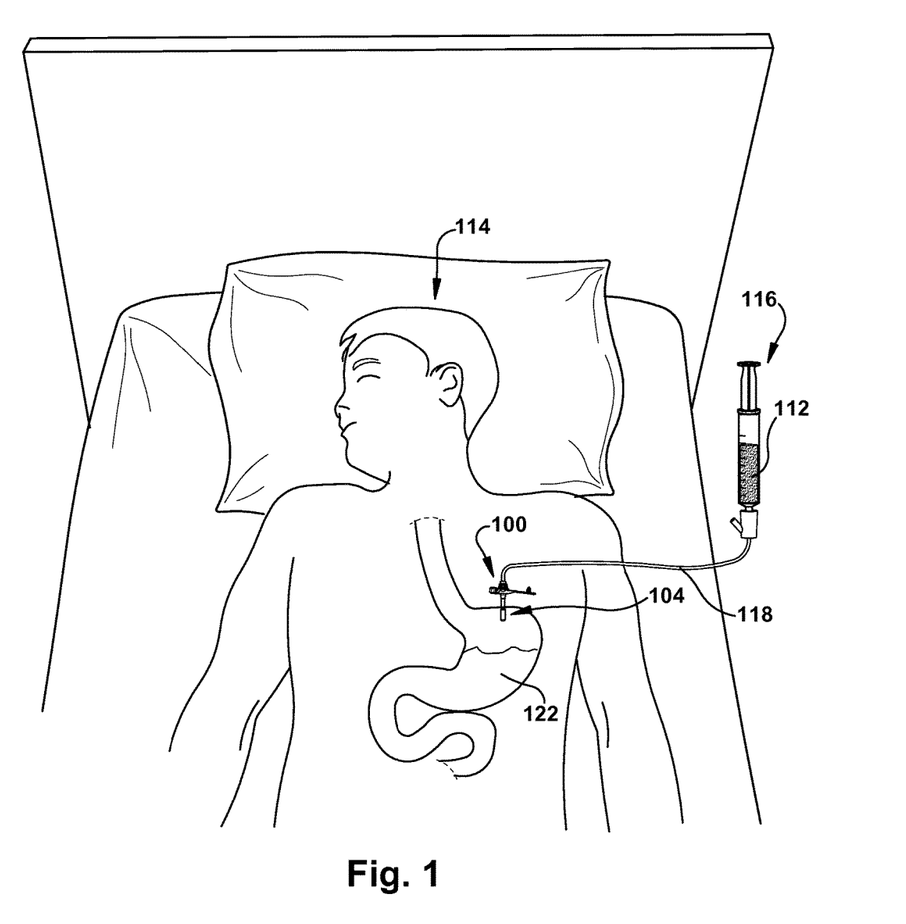
FIG. 1 illustrates enteral feeding of a patient using an embodiment of the invention described herein.
Figure 2A:
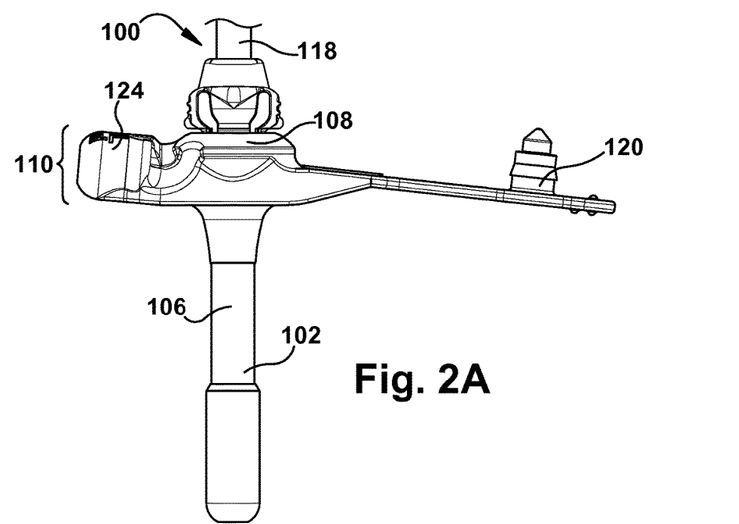
FIG. 2A illustrates an enlarged view of a button and interlock coupling adapter used in FIG. 1.

FIG. 1 illustrates the use of an embodiment of the interlock adapter 100 described herein. A button 102 is inserted into a patient's stoma 104, which provides a pathway to the patient's stomach 122. As shown in FIG. 2A, the button comprises a conduit 106 that leads from an opening 108 in the button base 110, where a medical fluid 112 is delivered to a patient 114. When in use, the interlock adapter 100 connects a feeding source 116 with the button base 110. The feeding source 116 may either be a bolus feeding or continuous drip feeding provided by a tubing 118 which connects to the button base 110. The interlock adapter 100 provides a secure, flexible connection between the feeding source 116 and the patient 114 to ensure proper delivery of the fluid 112 and to prevent leakage. Once the interlock adapter 100 is secured, the fluid 112 may pass from the feeding source 116, through the feed tubing 118, into the conduit 106, and finally to the patient 114. Various embodiments of the interlock adapter 100 will be described in more detail below.

The button base 110 also includes a safety plug 120 extending outwardly from the opening 108 and which may be folded over the opening 108 to plug the conduit 106. When the safety plug 120 is inserted into the conduit 106 (i.e., the conduit 106 is plugged), gastric leakage can be minimized or prevented. Plugging the button 102 can also help prevent unwanted germs, debris, particles, and the like from entering the stoma 104 and stomach 122 or otherwise contaminating the conduit 106. Some buttons 102 may further comprise a balloon (not shown) that may be inflated underneath the skin or in the stomach cavity 104 to help keep the button 102 in place. In such embodiments, a balloon valve tube line 230 is located extending outwardly from the button base 110, through which water or air may flow to inflate the balloon.

Figure 2B:
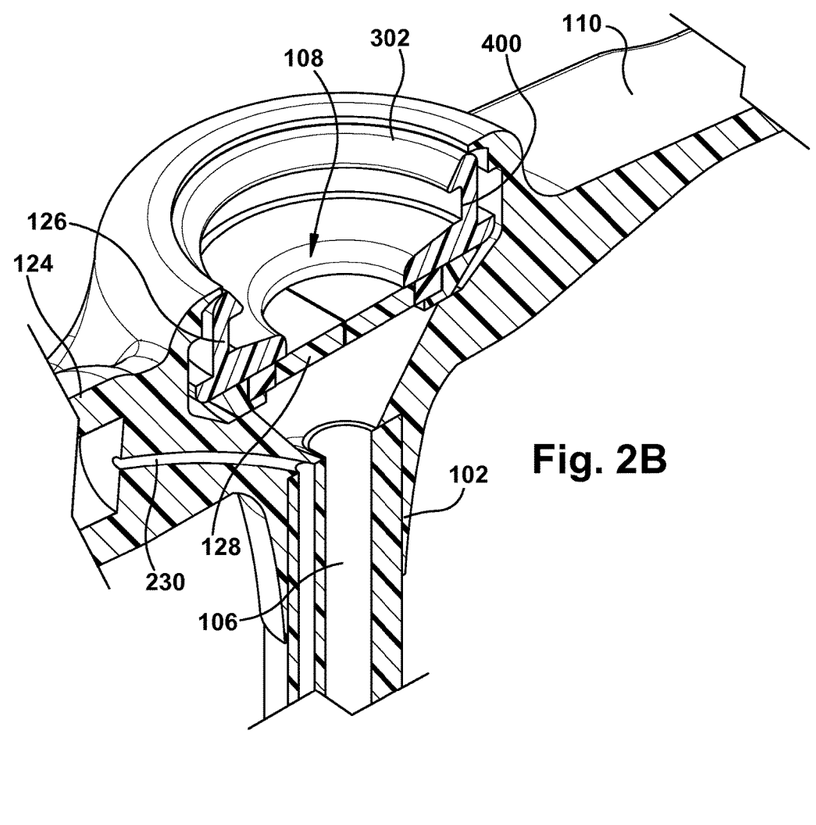
FIG. 2B illustrates a cross-section of the button and interlock coupling adapter of FIG. 2A.

The button base 110 may also comprise an external bolster 124 opposite the safety plug 120 to help maintain the button's position and balance when inserted in the stoma 104. In addition, the opening 108 of the button 102 and the button base 110 can comprise a one-way valve 128 to prevent stomach contents from leaking out of the tube. This is shown in FIG. 2B. The one-way valve 128 may only open when an interlock adapter is in place. An interlock ring (or locking ring) 126 for receiving the interlock adapter 100 is also located in the opening 108, above the one-way valve 128. The interlock ring 126 is recessed within the opening 108 so as to prevent any protruding elements from the button 102 or button base 110. However, in other embodiments, it may be desirable for an upper portion of the interlock ring 126 to protrude from the button base 110.

The interlock ring 126 may be offered pre-assembled in the button base 110, such that during the manufacture of the button 102, the interlock ring 126 is recessed into the opening 108 of the button base 110. Alternatively, it may be inserted post-manufacturing by an end user. When inserted post-manufacturing, it may be desirable to adhere the interlock ring 126 to the button base 110 using a suitable adhesive material, or the interlock ring 126 may also be held in the button base 110 by pressure and friction (for example, if the opening 108 of the button base 110 must be stretched to accommodate an interlock that is larger than the opening 108). In some embodiments, the interlock ring 126 is made of a rigid or hard material, such as a plastic type of material with sufficient rigidity to perform as described herein, while the button 102 and button base 110 are made of a softer, rubbery-like or more flexible material, such as silicone. However, any combination of medically safe materials is envisioned to be within the scope of the present invention.

Figure 3:
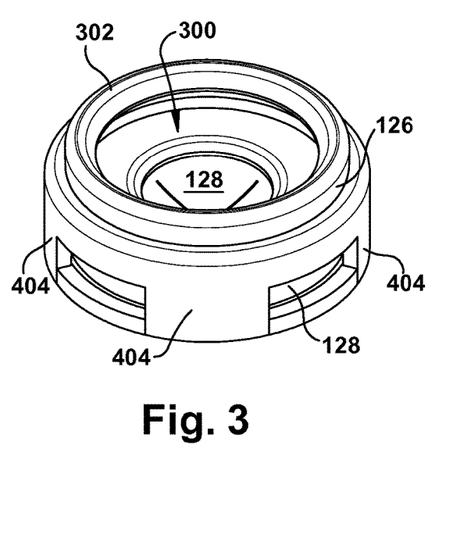
FIG. 3 illustrates a perspective view of an embodiment of an interlock and one-way valve.
Figure 4:
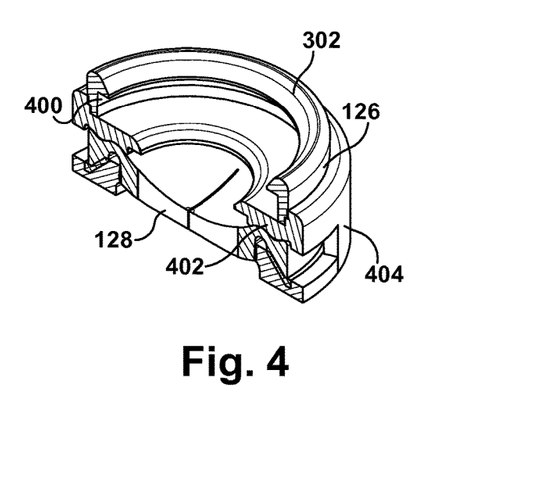
FIG. 4 illustrates a cross-section of the embodiment of FIG. 3.
Figure 4A:
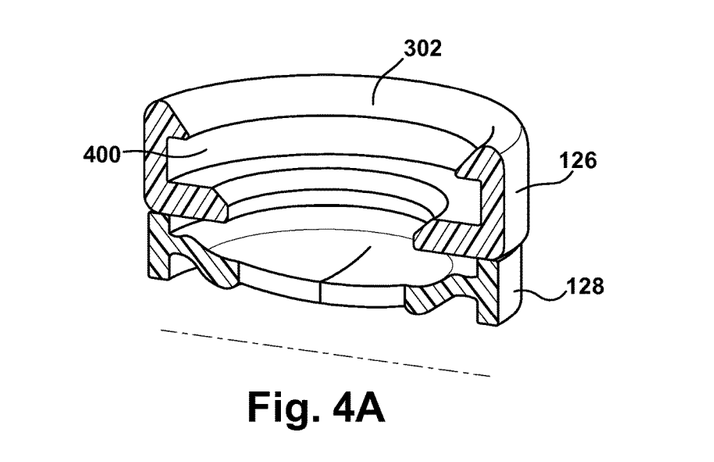
FIG. 4A illustrates a cross-section of an alternative embodiment to that of FIGS. 3 and 4.

Turning now to FIGS. 3, 4, and 4A, the interlock ring 126 and one-way valve 128 are shown in relation to each other from perspective and cross-sectional views, respectively. As can be seen in FIGS. 3 and 4, the interlock ring 126 sits on a support 402 comprising vertical portions 404 and a horizontal portion which forms an opening 300, and the opening 300 exposes the one-way valve 128 through the opening 108 of the button base 110. The vertical portions 404 extend for the height of the one-way valve 128, thereby providing further structural integration and protection of the interlock ring 126 with the one-way valve 128. As can be seen in the cross-sectional views of FIGS. 4 and 4A, the interlock ring 126 also comprises a recess 400 circumferentially around the inner wall that forms the opening 300. The recess 400 acts as a locking mechanism when an adapter, such as the adaptor 100 in FIG. 2A, is connected, which is described in more detail below. The top edge 302 of the interlock ring 126 may be beveled as illustrated to ease the insertion of the feed set adapter, thus reducing an amount of pressure exerted on a patient. In some embodiments, the interlock ring 126 and support 402 with vertical portions 404 may be manufactured as a single or combined component. In the embodiment shown in FIG. 4A, the interlock ring 126 is a single molded unit with the beveled upper edge 302 and the recess 400 circumferentially around the inner wall and sits directly above the one-way valve 128.

Figure 5:
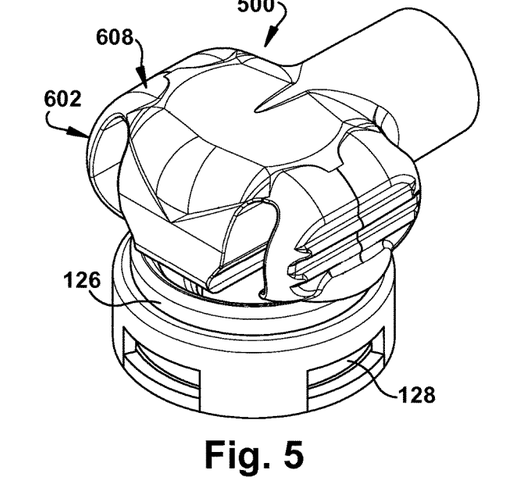
FIG. 5 illustrates a perspective view of an embodiment of a right angle feed set adapter connected to an interlock ring assembly (with one-way valve)
Figure 5A:
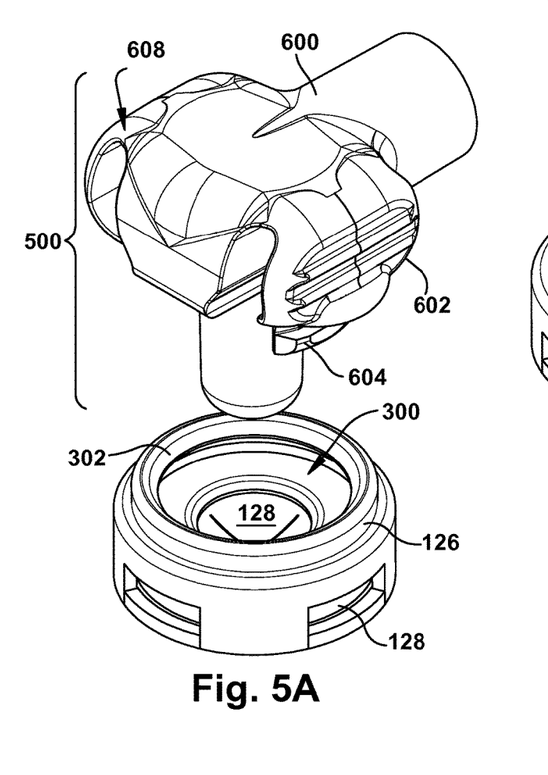
FIG. 5A illustrates another perspective view of the right angle feed set adapter disconnected from an interlock ring assembly.
Figure 5B:
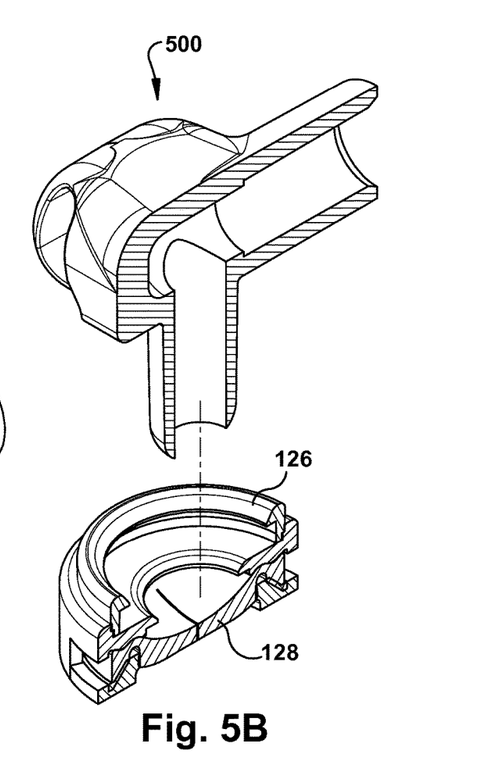
FIG. 5B illustrates a cross section of the perspective view of FIG. 5A.
Figures 6, 6A:
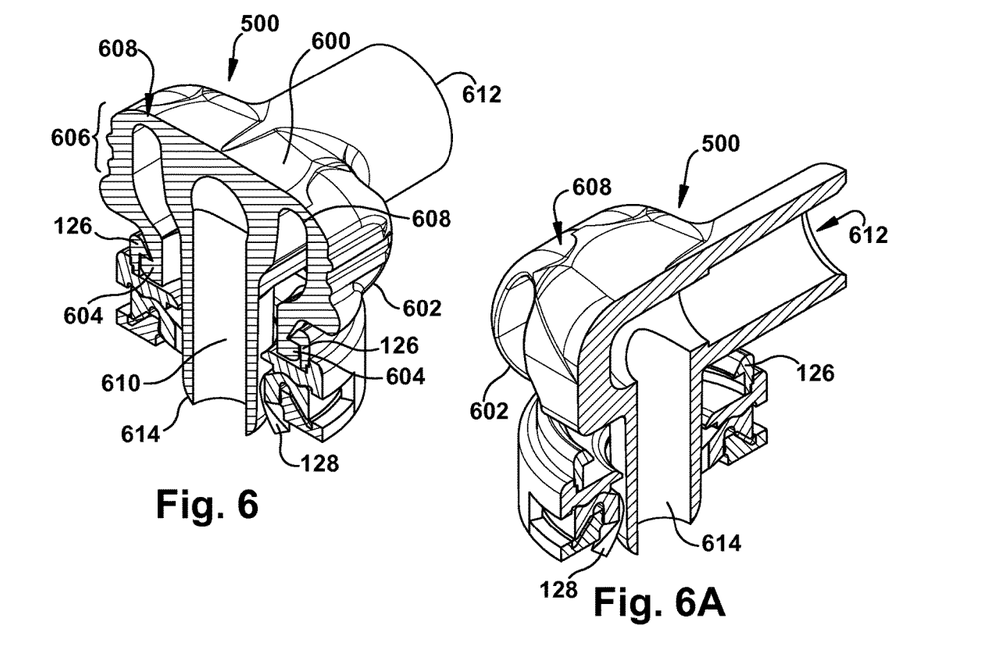
FIG. 6 illustrates a cross-section of the embodiment of FIG. 5.
FIG. 6A illustrates another cross-section of the embodiment of FIG. 5.

FIGS. 5, 5A, 5B, 6, and 6A illustrate perspective and cross-sectional views of a right-angle adapter 500 and the interlock ring 126 with the one-way valve 128. Specifically, FIG. 5 illustrates a perspective view of the right angle adapter 500 connected to the interlock ring 126 and inserted into the one-way valve 128, while FIGS. 5A and 5B illustrate perspective and cross-section views, respectively, of the right angle adapter 500 not connected to the interlock ring 126. FIGS. 6 and 6A illustrate cross-sectional views of the right angle adapter 500 connected to the interlock ring 126 and inserted into the one-way valve as shown in FIG. 5.

With reference to these figures, the right angle adapter 500 comprises a rigid body 600 made from a plastic or other rigid material. The rigid body 600 has flexible arms 602 hinged (at 608) on opposite sides of the rigid body 600. The hinged flexible arms 602 are continuous with the rigid body 600 such that the connection between the hinged flexible arms and the rigid body is seamless and of the same material. Put another way, the rigid body 600 includes two hinges 608 that are continuous with and extend outward from the rigid body 600. Each hinge extends into a flexible arm 602 that is effectively a continuation of the rigid body 600. That is, the flexible arms 602 are attached to the rigid body 600 at the hinge 608; and there is space between a substantial portion of each flexible arm 602 and the rigid body 600 of the adapter 500 to allow each hinge 608 to flex and give movement to each flexible arm 602. When the flexible arms 602 are depressed, there remains a space between the flexible arms 602 and the rigid body 600 that is effectively created by the hinge 608 and the flexible arms 602 flex inward by way of the hinge 608.

Each flexible arm 602 comprises a locking protrusion 604 at the end of the arm 602 opposite where it is hinged. In some embodiments, these locking protrusions 604 may be beveled. In this way, when the beveled edge of the locking protrusions 604 contacts the beveled edge 302 of the interlock ring 126, the locking protrusions 604 can slide into the opening 300 of the interlock ring 126 and fit into the recess 400 of the interlock ring 126, thereby locking the adapter 500 within the interlock ring 126. Because the recess 400 of the interlock ring 126 is located circumferentially around the interlock ring 126, the adapter 500 (by way of the locking protrusions 604) may rotate freely around the interlock ring 126, while remaining connected together. The flexible arms 602 may also comprise ridges 606 to increase or improve grip. For example, to insert the adapter 500 into the interlock ring 126, a user may securely grip the flexible arms 602 and push the adapter 500 into the interlock ring 126. To disconnect, the user can squeeze the flexible arms 602, thereby moving the locking protrusions 604 inward and clearing the locking protrusions 604 of the recess 400 of the interlock ring 126. The adapter 500 may then be withdrawn from the interlock ring 126.

The adapter 500 also comprises a pathway 610 between an input port 612 and output port 614 such that a medical fluid may be passed into the input port 612 and out the output port 614 through the pathway 510. As illustrated, the output port 614 protrudes beyond the rigid body 600 and flexible arms 602 of the adapter 500, such that when the adapter 500 is connected to the interlock ring 126, the output port 614 penetrates and opens the one-way valve 128 of the button. That is, once connected, a medical fluid may be delivered to the input port 612 of the adapter 500 and through the conduit 106 of the button 102. As shown, the input and output ports 612, 614 are perpendicular to each other. Therefore, the pathway between the input and output ports 612, 614 creates a right angle.

Figure 7:
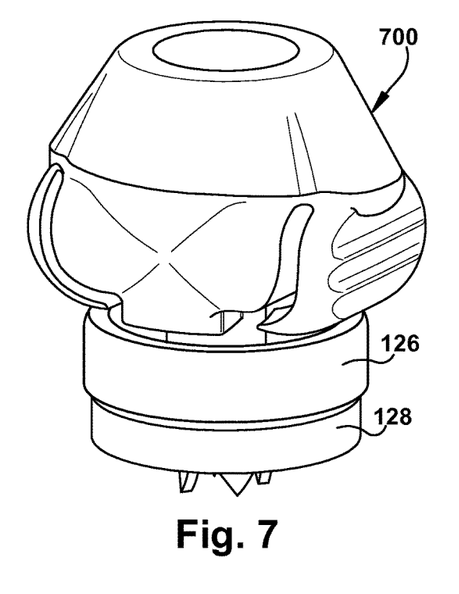
FIG. 7 illustrates a perspective view of an embodiment of a straight interlock feed set adapter coupled to an interlock ring assembly.
Figure 8:
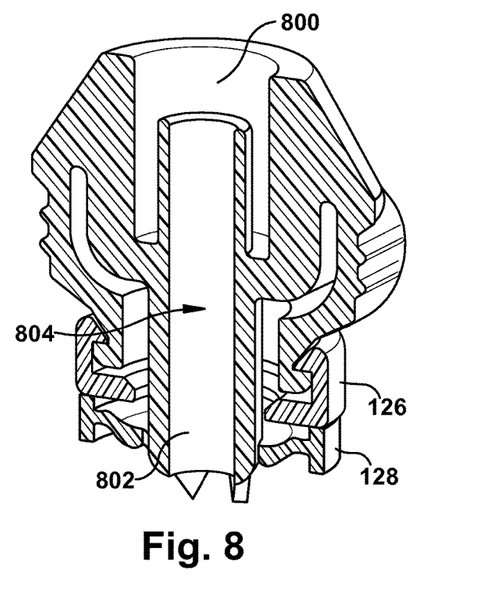
FIG. 8 illustrates a cross-section of the embodiment of FIG. 7.

FIGS. 7 and 8 illustrate an adapter substantially similar to the one illustrated and described in FIGS. 5, 5A, 6, and 6A however, the embodiment of FIGS. 7 and 8 shows a straight adapter 700. That is, rather than the input and output ports being at right angles requiring an angled pathway, the straight adapter 700 has an input port 800 above an output port 802 such that a pathway 804 between the input and output ports 802, 804 is straight.

Figures 9, 9A:
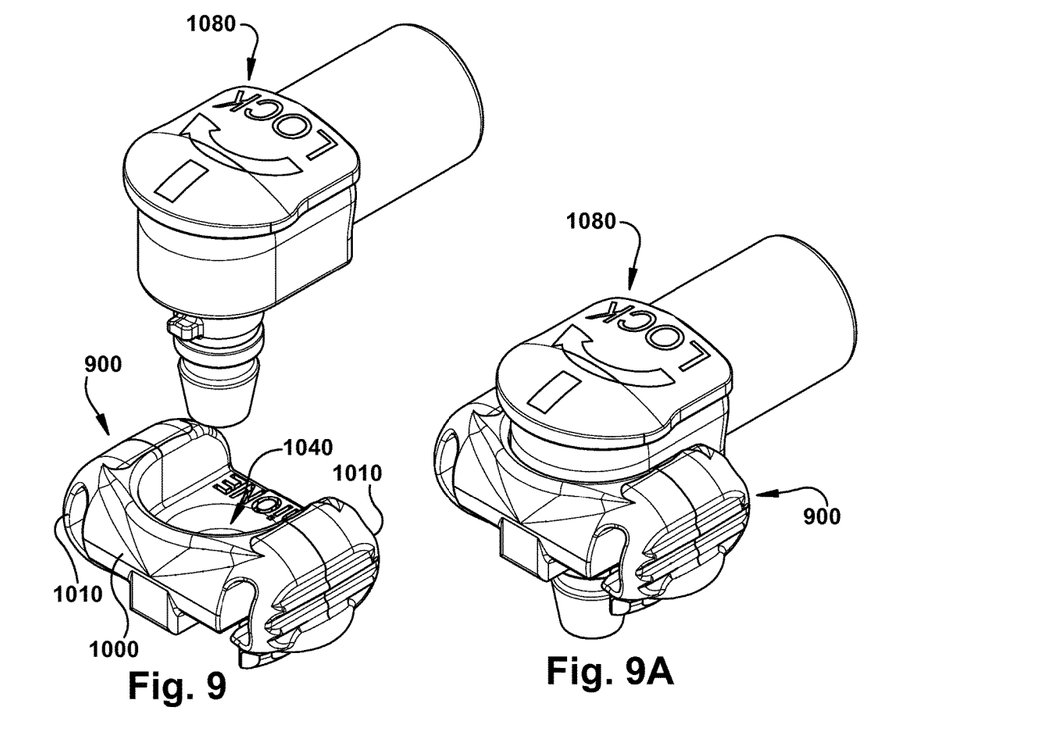
FIG. 9 illustrates a perspective view of an embodiment of a conversion adapter before being connected to a pre-existing feed set adapter.
FIG. 9A illustrates a conversion adapter connected to a pre-existing feed set adapter.
Figure 10:
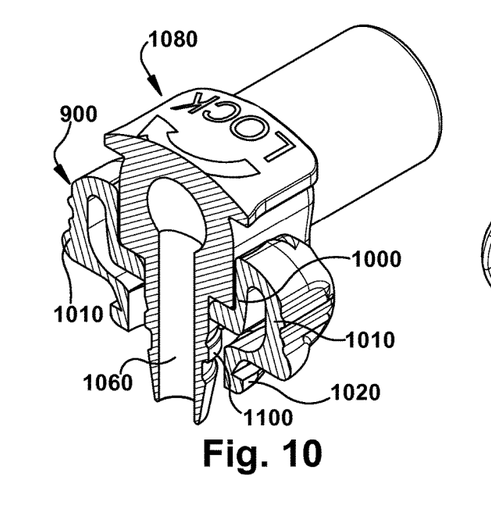
FIG. 10 illustrates a cross-section of the embodiment of FIG. 9A.
Figure 10A:
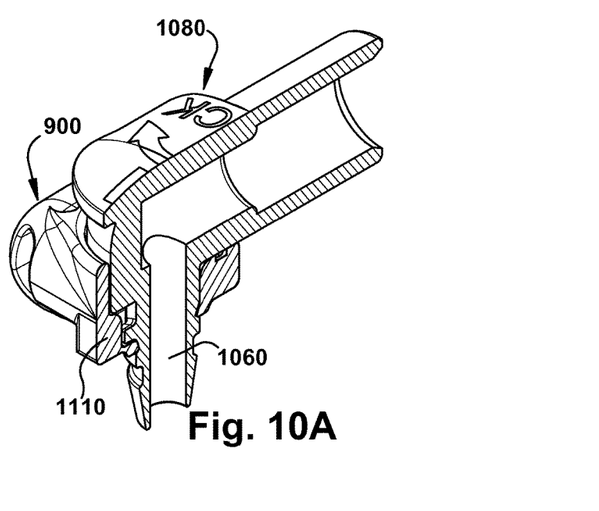
FIG. 10A illustrates another cross-section of the embodiment of FIG. 9A.

Finally, FIGS. 9, 9A, 10, and 10A illustrate a conversion interlock adapter 900 of the present invention. The adapter 900 is usable with pre-existing feed set adapters in order to couple the feed set adapter to an interlock ring assembly (in a button). The adapter 900 comprises a rigid frame 1000 having hinged flexible arms 1010 extending continuously and seamlessly therefrom and locking protrusions 1020 at the end of each arm similar to that described above in FIGS. 5-8. The hinged arms flex inward to engage or disengage from an interlock ring. The rigid frame 1000 includes an opening 1040 to receive a separate, pre-existing feed set adapter having input and output ports and a pathway for fluid to flow. An output port 1060 of the pre-existing adapter 1080 may be inserted through the opening 1040 of the rigid frame 1000 and locked into place by mating the ridges 1100 that encircle a portion of the output port 1060 of the pre-existing adapter 1080 with complimentary ridges 1110 on the conversion interlock adapter 900. Therefore, whereas the adapters illustrated in the embodiments of FIGS. 5-8 are manufactured as a unitary piece, for example, by plastic molding, the conversion interlock adapter 900 of FIGS. 9-10 is separable from the pre-existing adapter 1080.

It should also be noted that the adapter and interlock in any of the above embodiments may be manufactured from or coated with a glow in the dark material. Therefore, the interlock and adapter may be more easily visible in the dark.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. An interlock adapter connector set for providing a medical fluid to a patient, comprising:
   a rigid body, the rigid body comprising:
      an input port, an output port, and a pathway between the input and output ports through which the medical fluid flows through the rigid body; and
      at least two flexible arms extending continuously from the rigid body creating a hinge on one end of each arm and comprising a locking protrusion at an opposite end of each arm,
      wherein when the flexible arms are depressed inward about the hinge, the locking protrusions of the flexible arms also flex inward; and
   a button comprising:
      a button base with an opening; and
      an interlock ring inset in the opening of the button base, the interlock ring comprising an upper edge recessed within the opening of the button base, an inner circumferential wall of the upper edge defining an opening of the interlock ring,
      wherein the interlock ring comprises an inner wall having a recess extending circumferentially around the inner wall such that an entirety of the inner wall is recessed from the opening of the interlock ring, and the recess and the inner wall extend circumferentially and continuously around the button base,
   wherein the rigid body is capable of mating with the interlock ring by way of the locking protrusions such that the locking protrusions securely sit within the recess of the interlock ring when mated, and
   wherein the locking protrusions are freely rotatable within the recess when mated such that the rigid body is freely rotatable circumferentially and continuously around the button.

2. The interlock adapter connector set of claim 1, wherein depressing the at least two flexible arms releases the rigid body from the interlock ring to unmate the rigid body from the interlock ring.

3. The interlock adapter connector set of claim 1, wherein the rigid body and interlock ring are made from a rigid material and the button base is made from silicone.

4. The interlock adapter connector set of claim 1, wherein the interlock adapter connector set comprises a material that glows in the dark.

5. The interlock adapter connector set of claim 1, wherein when the rigid body is mated with the button, the output port penetrates a valve located within the button base.

6. The interlock adapter connector set of claim 1, wherein a space exists between a substantial portion of each flexible arm and the rigid body which allows movement of each flexible arm about each hinge.

7. The interlock adapter connector set of claim 1, wherein the rigid body and the flexible arms hinged to the rigid body are a single, continuous molded unit.

8. The interlock adapter connector set of claim 1, wherein when the rigid body is mated with the button, the hinge on each arm is exterior to the opening of the button.

* * * * *